(12) United States Patent
Porwancher

(10) Patent No.: US 8,694,265 B2
(45) Date of Patent: Apr. 8, 2014

(54) BIOINFORMATIC APPROACH TO DISEASE DIAGNOSIS

(75) Inventor: Richard Porwancher, Princeton, NJ (US)

(73) Assignee: Richard Porwancher, Princeton, NJ (US)

( * ) Notice: Subject to any disclaimer, the term of this patent is extended or adjusted under 35 U.S.C. 154(b) by 0 days.

(21) Appl. No.: 13/184,017

(22) Filed: Jul. 15, 2011

(65) Prior Publication Data

US 2011/0295516 A1 Dec. 1, 2011

Related U.S. Application Data

(62) Division of application No. 11/852,283, filed on Sep. 8, 2007, now Pat. No. 8,005,627.

(60) Provisional application No. 60/824,980, filed on Sep. 8, 2006.

(51) Int. Cl.
*G06F 7/00* (2006.01)

(52) U.S. Cl.
USPC ............ 702/20; 702/19; 703/11; 703/12; 707/700; 424/184.1; 436/501

(58) Field of Classification Search
None
See application file for complete search history.

(56) References Cited

U.S. PATENT DOCUMENTS 7,879,569 B2 * 2/2011 Moore et al. ............... 435/7.23

FOREIGN PATENT DOCUMENTS

WO WO2006052842 * 1/2006

* cited by examiner

*Primary Examiner* — Mary Zeman
(74) *Attorney, Agent, or Firm* — Ballard Spahr LLP

(57) ABSTRACT

A kit and test panel utilizing a multivariate diagnostic method based on optimizing diagnostic likelihood ratios through the effective use of multiple diagnostic tests is disclosed. The Neyman-Pearson Lemma provides a mathematical basis to produce optimal diagnostic results. The method can comprise identifying those tests optimal for inclusion in a diagnostic panel, weighting the result of each component test based on a multivariate algorithm described below, adjusting the algorithm's performance to satisfy predetermined specificity criteria, generating a likelihood ratio for a given patient's test results through said algorithm, providing a clinical algorithm that estimates the pretest probability of disease based on individual clinical signs and symptoms, combining the likelihood ratio and pretest probability of disease through Bayes' Theorem to generate a posttest probability of disease, interpreting that result as either positive or negative for disease based on a cutoff value, and treating a patient for disease if the posttest probability exceeds the cutoff value.

12 Claims, 3 Drawing Sheets

BIOINFORMATIC APPROACH TO DISEASE DIAGNOSIS

CROSS-REFERENCE TO RELATED APPLICATIONS

The present application claims priority to, and is a divisional of U.S. patent application Ser. No. 11/852,283, filed Sep. 9, 2007, which in turn claims priority to U.S. Provisional Patent Application Ser. No. 60/824,980, filed Sep. 8, 2006, the disclosures of which are incorporated herein by reference.

GOVERNMENT SUPPORT CLAUSE

This invention was made with government support under Grant No. 1R43AI069564-01 which was awarded by the National Institute of Allergy and Infectious Diseases (NI-AID). The government has certain rights in the invention.

BACKGROUND OF THE INVENTION

The present invention relates to methods for constructing multivariate predictive models to diagnose diseases for which current test methods are considered inadequate in either sensitivity or specificity. In particular, the present invention relates to predictive models for diagnosing diseases with a combination of laboratory tests, generating specificities of at least 80%.

More particularly, the present invention relates to the construction of a multivariate predictive model for diagnosing Lyme disease (LD) by choosing the best tests from among those currently available, utilizing the raw data produced by these tests instead of the manufacturers' binary test results, combining the test values into a single score through a special statistical function, weighting the importance of each component of the function when producing the score, generating a likelihood ratio from each patient's score, determining the pretest probability of disease through a special algorithm utilizing individual clinical signs and symptoms, combining the likelihood ratio with the pretest probability of disease through Bayes' Theorem to produce a posttest probability of disease, and determining a posttest probability cutoff point through a prospective validation study of the multivariate predictive model, against which individual patients' test results can be interpreted as indicative Lyme disease or not. The present invention also relates to component laboratory tests identified by the predictive model as critical for diagnosis in the form of test kits with the test panel components incorporated into a microtiter plate to be analyzed by a commercial laboratory.

Since the discovery that the spirochete *Borrelia burgdorferi* was the cause of LD over 25 years ago, numerous tests have been developed to detect this organism. Direct cultures of tissue or body fluids are possible, but suffer from low sensitivity. Direct detection methods involve assays for a component of *B. burgdorferi* or the DNA itself. Most PCR tests for *B. burgdorferi* DNA are insensitive, such as plasma, serum, whole blood, urine, and spinal fluid. Although invasive, arthrocentesis and skin biopsies often detect DNA by PCR in acute cases, aiding diagnosis. Performing skin biopsies is unnecessary under most circumstances because a well-trained physician can usually diagnose the characteristic rash, erythema migrans, by visual inspection alone.

Patients presenting with neurological symptoms or chronic arthritic symptoms will usually not benefit from PCR tests for *B. burgdorferi* DNA. In the latter cases, serological tests for antibody for *B. burgdorferi* are commonly used. Numerous methods have been employed, including whole-cell EIA, capture-EIA, peptide-antigen EIA, recombinant protein EIA, immunofluorescent antibody, immunodot, and immunoblots to detect IgG, IgM, and IgA antibodies. All serological methods may lead to false-positive results; however the most common test for *B. burgdorferi* anti-body, the whole-cell EIA, is particularly susceptible to false-positive results. Therefore the CDC has advised a two step process to confirm antibody: first test serum by whole-cell EIA or an equivalent method, then use a highly specific immunoblot to confirm those results positive or indeterminate by the first step.

Most antibody methods are insensitive early in the disease (<4 weeks), but become more sensitive after the first few weeks have passed. This lack of sensitivity for early disease and a high rate of false-positive serology have undermined public confidence in the two-step process. The CDC and NIH have conducted active research programs for better diagnostic tests. The most promising of these new tests have been the recombinant and peptide-antigen EIAs; these tests exhibit sensitivity and specificity similar to the prior two-step process, but embodied in a single test.

The concept of a single test is the most appealing and some experts have advocated using C6 IgG as an alternative to the two-step method. The lack of sensitivity in early disease persists (at least 40% false-negative rate) with this new generation of tests (including C6 IgG), leading to recommendations for alternative interpretive algorithms by some physicians and Lyme advocacy groups. Western immunoblots using alternative interpretive algorithms (Donta, *Clin. Infect. Dis.*, 25 (Suppl. 1), S52-56 (1997)) have demonstrated better sensitivity, but much worse specificity (up to 40% false-positives). This trade-off between sensitivity and specificity is a well recognized limitation in diagnostic testing.

The use of multiple tests in combination is not new. The two-step algorithm is borrowed from the literature on syphilis and HIV testing: a sensitive but non-specific screening test is confirmed by a more specific test. Implicit in this paradigm is the knowledge that the second, confirmatory test is at least as sensitive as the screening test. This analogy breaks down for LD (Trevejo et al., *J. Infect. Dis.*, 179(4), 931-8 (1999). The Western blot, though specific, is not as sensitive for early disease as the EIA test. The improved specificity of the two-step method is offset by limited sensitivity.

Tests are used in combination to gain either sensitivity or specificity; interpretive rules are usually generated through Boolean operators. If the "OR" operator is used, then a combination test is positive if either component is positive. If each component detects a different antigenic epitope of *B. burgdorferi*, then a test fashioned using the "OR" operator will likely be more sensitive than any individual component. However, each new component also has its own intrinsic rate of false-positive reactions. Overall false positive rates increase linearly when using the "OR" operator combinations (Porwancher, *J. Clin. Microbiol.* 41(6), 2791 (2003)). If the "AND" operator is used, then a test is positive only when both components are positive; this operator is used to improve the specificity of a given combination of tests, often at the expense of sensitivity.

When using the "AND" operator, a counterintuitive event may occur: additional antigens can be used to improve specificity without loss of sensitivity. This effect has been demonstrated for E1pB1 and OspE; when FlaB and OspC were added to the mix; requiring multiple antibody responses actually improved specificity from 89% to 98%, while maintaining sensitivity (Porwancher, *J. Clin. Microbiol.*, (2003)). Sensitivity was maintained because there were 15 new ways for antibody combinations to form when two new antigens were added; patients with disease tend to have multiple positive antibody combinations. Specificity improved because false-positive combinations are rare, even though there are more ways for these to form.

Bacon et al., *J. Infect. Dis.*, 187, 1187-1199 (2003) evaluated using two peptide or recombinant antigens together in binary form and assigned equal importance to antibodies generated by either antigen. The authors used the Boolean "OR" operator, evaluating several different antibody combinations and settled on two pairs of antibodies for diagnosis, either C6 IgG and pepC10 IgM or V1sE1 IgG and pepC10 IgM. While the 2-tier method using a VIDAS whole-cell EIA was included, no other recombinant antigens were evaluated. By limiting the choice of antigens and not weighting the ones that are included, this method compromises test performance.

Western blots are basically multiple binary test observations: a band is formed when antibody and antigen mix together in a clear electrophoretic gel, creating a visible line. Antibody is either observed or not. Of the 10 key antibodies detected by IgG Western blot, we do not know which antibody results contribute independent information to diagnosis. Nor is the information weighted according to its level of importance; all positive components are weighted the same. Failing to weight the importance of individual bands might have led to requiring an excessive number of bands to confirm disease, thus limiting sensitivity.

Honegr et al., *Epidemiol. Mikrobiol. Immunol.*, 50(4), 147-156 (2001), interpreted Western blots using logistic regression analysis. While directed toward human diagnosis, the study tried to determine the optimal use of different species of *B. burgdorferi* to utilize in European tests, as well as determine interpretive criteria. Band results reported in binary fashion were used to create a quantitative rule; however, no likelihood ratios were reported from this regression technique, no partial ROC areas were maximized using the logistic method [as in McIntosh and Pepe (2002)], there were no specificity goals for ROC areas, and there was no attempt to utilize clinical information. While key Western blot bands were identified, and weighted, the failure to use clinical information, set specificity goals, or to maximize likelihood ratios (and therefore partial ROC areas) raises a question about the validity of the rules that were derived (according to the Neyman-Pearson Lemma).

Robertson et al., *J. Clin. Microbiol.*, 38(6), 2097-2102 (2000), performed a study whose purpose was similar to Honegr et al. However Robertson et al. did not produce a quantitative rule as a consequence of utilizing multiple Western blot bands. While significant bands were identified through logistic regression, they utilized this information in a binary fashion and generated interpretive rules using either two or three of the bands so identified. There was no attempt to weight the importance of individual bands. In the end, the purported rules developed by logistic regression were no better than pre-existing interpretive criteria. No likelihood ratios were generated, no ROC curves, and no clinical information was utilized. There was no attempt to use the Western blot with other tests. Their failure to quantify their results severely limited its use.

Guerra et al., *J. Clin. Microbiol.*, 38(7), 2628-2632 (2000), studied the use of log-likelihood analysis of Western blot data in dogs. The emphasis of her study was to develop a rule to diagnose Lyme disease in dogs that had received the Lyme disease vaccine (known to interfere with diagnosis). Guerra did produce a quantitative rule based on likelihood ratios. She combined this rule with epidemiological data to generate posttest probabilities. None of the animals were sick. No ROC analysis was performed, nor was there an attempt to determine the specificity or sensitivity of the technique. While a predictive rule could be generated, its performance was unclear because the epidemiological data was poorly utilized.

As demonstrated above, the LD field is limited by the lack of a theoretical basis for test strategy. There has been remarkably little work done using multivariate analysis and Lyme disease. Multiple tests exist to diagnose LD, but little is known about which tests are optimal or how to use tests together to enhance diagnostic power. U.S. Pat. No. 6,665,652 described an algorithm that enabled diagnosis of LD using multiple simultaneous immunoassays; this method required that the antibody response to antigens selected for diagnostic use be highly associated with LD (i.e. few false-positive results) and conditionally independent among controls. The disclosure of the above patent, particularly as it relates to LD diagnosis, is incorporated herein by reference.

Diagnostic methods are usually compared based on misclassification costs (utility loss), a value tied to the prevalence of LD in the general population. While the dollar cost of diagnostic tests is one means to compare outcomes, another and possibly more important goal is to estimate the loss of productive life (regret) from a given outcome. The two factors that generate regret are false-negative and false-positive serology.

The cost associated with false-negative results is the difference in regret between those with false-negative and true-positive serology, for which the increased personal, economic, and social cost of delaying disease treatment are factors. The cost associated with false-positive results is the difference in regret between those with false-positive and true-negative serology, for which the personal, economic, and social costs of administering the powerful intravenous antibiotics to healthy patients are all factors.

The foregoing issues also exist for many other infectious and non-infectious diseases. There remains a need for a predictive model that enables the selection of the fewest number of tests that contribute significantly to disease diagnosis, thereby limiting the cost of testing without sacrificing diagnostic sensitivity.

SUMMARY OF THE INVENTION

This need is met by the present invention. A multivariate diagnostic method based on optimizing diagnostic likelihood ratios through the effective use of multiple diagnostic tests is proposed. The Neyman-Pearson Lemma (Neyman and Pearson, *Philosophical Transactions of the Royal Society of London, Series A*, 231, 289-337 (1933)) provides a mathematical basis for relying on such methods to produce optimal diagnostic results. When individual diagnostic tests for a disease prove inadequate in terms of either sensitivity or specificity, the present invention provides a method for combining existing tests to enhance performance.

The method includes the steps of: identifying those tests optimal for inclusion in a diagnostic panel, weighting the result of each component test based on a multivariate algorithm described below, adjusting the algorithm's performance to satisfy predetermined specificity criteria, generating a likelihood ratio for a given patient's test results through said algorithm, providing a clinical algorithm that estimates the pretest probability of disease based on individual clinical signs and symptoms, combining the likelihood ratio and pretest probability of disease through Bayes' Theorem to generate a posttest probability of disease, interpreting that result as either positive or negative for disease based on a cutoff value, and treating a patient for disease if the posttest probability exceeds the cutoff value.

Therefore, according to one aspect of the present invention, a method is provided for constructing a multivariate predictive model for diagnosing a disease for which a plurality of test methods are individually inadequate, wherein the method includes the following steps:

(a) performing a panel of laboratory tests for diagnosing said disease on a test population including a statistically significant sample of individuals with at least one objective sign of disease and a statistically significant control sample of healthy individuals and persons with cross-reacting medical conditions;

(b) generating a score function from a linear combination of the test panel results, wherein the linear combination is expressed as $\beta^T Y$, wherein D is the disease; $Y_1, \ldots, Y_k$ is a set of K diagnostic tests for D; Y is a vector of diagnostic test results $\{Y_1, \ldots, Y_k\}$; D'=not D; $\beta$ is a vector of coefficients $\{\beta_1, \ldots, \beta_k\}$ for Y; and $\beta^T$ is the transpose of $\beta$;

(c) performing a receiver operating characteristic (ROC) regression or alternative regression technique of the score function, wherein the test panel is selected and $\beta$ coefficients are calculated simultaneously to maximize the area under the curve (AUC) of the empiric ROC as approximated by:

$$AUC(\beta) = \frac{1}{n^D \cdot n^H} \sum_{i \in D, j \in H} I(\beta^T Y_i > \beta^T Y_j),$$

wherein I is a sigmoid function, N=the number of study subjects, $n^D$ in the number of patients with disease D, $n^H$ is the number of healthy controls, $n^D + n^H = N$; $i=1, \ldots, n^D$, $i \in D$ are patients with disease; $j=1, \ldots, n^H$, $j \in H$ are healthy controls;

(d) calculating for each individual the pretest odds of disease; generating a diagnostic likelihood ratio of disease by determining the frequency of each individual's test score in said diseased population relative to said control population; and multiplying the pretest odds by the diagnostic likelihood ratio to determine the post-test odds of disease for each individual;

(e) converting a set of posttest odds into posttest probabilities and creating an ROC curve by altering the posttest probability cutoff value;

(f) comparing the ROC areas generated by one or more regression techniques to determine an optimal methodology comprising the tests to be included in an optimum test panel and the weight to be assigned each test score alone or in combination;

(g) dichotomizing the optimal methodology by finding that point on the final ROC graph tangent to a line with a slope of (1−p)·C/p·B, where p is the population prevalence of disease, B is the regret associated with failing to treat patients with disease and C is the regret associated with treating a patient without disease, thereby generating a posttest probability cutoff value; and (h) displaying the optimum test panel for disease diagnosis, the weight each individual test score is to be assigned alone or in combination, and the cutoff value against which positive or negative diagnoses are to be made.

When $t_0$ is the maximum false-positive rate desired by a physician interpreting the tests and is a multiple of $1/n^H$; then the $\beta$ coefficients and test panel are chosen simultaneously through partial ROC regression in order to generate the largest area below the partial ROC curve for the $(1-t_0)$ quantile of individuals without D, where $\beta^T Y_j > c$ and $S_H(c) = t_0$ (the survival function of patients without disease with a score of c). When several predictive models are under consideration, their partial AUC for the $(1-t_0)$ quantile are compared with that produced by partial ROC regression in order to determine the optimal technique (Dodd and Pepe, 2003).

Methods according to the present invention further include the steps of testing individual patient serum samples using the optimum methodology; reporting the diagnostic result to each patient's physician and treating those patients whose posttest probability exceeds the cutoff value for disease D. When the posttest probability falls below the cutoff value, but the illness is less than 2 weeks duration, the test should be repeated in 14 days in order to look for seroconversion.

Pretest risk can be determined using an individual's clinical signs and symptoms. In the event that there is insufficient data to determine the pretest risk that a patient has Lyme disease, then the laboratory may report the likelihood ratio for that patient's test results directly to the physician, as well as the cutoff value to distinguish positive from negative results. A diagnostic cutoff can be determined by observing the likelihood ratio which results in 99% specificity in a control population of patients.

The present invention has also identified significant roles for pepC10 IgM, V1sE1 IgG and C6 IgG antibodies in the diagnosis of LD, in combination with one other or with different antibodies. The present invention therefore also includes a test panel comprising a plurality of antibody tests, kit and methods for the detection of LD including one or more of these additional antibodies.

A computer-based method is also provided for diagnosing a disease for which a plurality of test methods are individually inadequate, which method includes the steps of combining weighted scores from a panel of laboratory test results chosen through the multivariate techniques described above, comparing the combined weighted results to a cutoff value, and diagnosing and treating a patient for disease D based on exceeding the cutoff level. The disease D can be Lyme disease. Computer-based methods include methods evaluating results from a test panel including at least one antigen test selected from V1sE1 IgG, C6 IgG, and pepC10 IgM antigen tests.

The inventive method reduces error because specificity requirements are satisfied; this requirement is particularly important for LD because of overdiagnosis and overtreatment for false-positive results. When the disease is LD, the tests chosen by the proposed method may be employed by the algorithm described in U.S. Pat. No. 6,665,652 after being dichotomized. Alternatively, these tests can be directly utilized by new methodologies for LD prediction.

Alternative multivariate methods, including but not limited to logistic regression, log-likelihood regression, linear regression, and discriminant analysis, can learn which features are optimal from ROC regression methods. The learning process is particularly valuable for diseases where high specificity is needed. These alternative methods cannot focus their regression methodology on a portion of the ROC curve. By learning the optimal test choices, they can rerun the regression analysis using these specific variables, thus maximizing their predictive power.

DETAILED DESCRIPTION OF PREFERRED EMBODIMENTS

Figure 1:
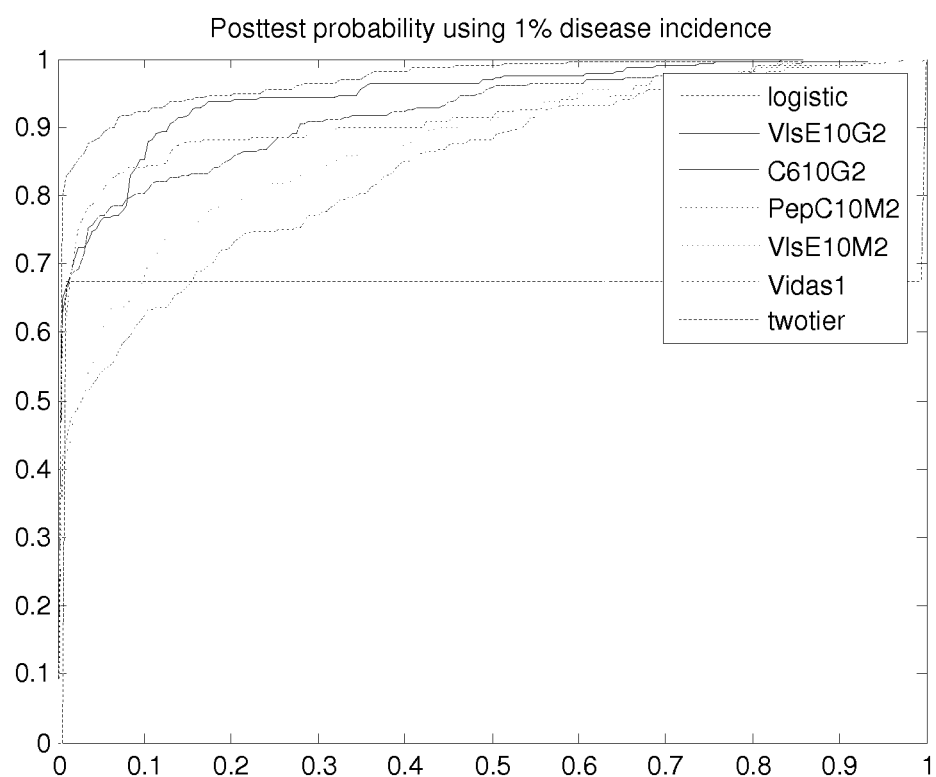
FIG. 1 depicts an ROC plot based on posttest probability assuming 1% incidence of disease for five Lyme Disease assays.

The LD field is limited by the lack of a theoretical basis for test strategy. Signal detection theory provides a theoretical basis to create rules to both include and weight the contribution of different tests. The likelihood ratio for a given set of test results is the probability that those results will be seen in patients with disease, divided by the probability that those same set of results will be seen in patients without disease. The Neyman-Pearson lemma (1933) states that the algorithm that produces the highest likelihood ratio for a given specificity is the optimal interpretive algorithm. This mathematical statement leads us to search for methods that will maximize the diagnostic likelihood ratio derived from a given set of tests.

ROC regression methods are the optimal methods to maximize likelihood ratios. (Pepe, *The Statistical Evaluation of Medical Tests for Classification and Prediction*, (First Edition ed. Oxford, U.K., Oxford University Press, 2003); Ma and Huang, *Regularized ROC Estimation: With Applications to Disease Classification Using Microarray*, (University of Iowa, Department of Statistics and Actuarial Science, Technical Report No. 345, 2005)). ROC curves are generated by varying the score cutoff values generated using a specific algorithm for a given set of tests. Sensitivity and specificity results follow from producing such cutoff values. An ROC curve quantifies the trade-off between sensitivity and specificity. It is not well known that the derivative of the ROC curve at any given specificity level is the likelihood ratio for that test cutoff value. Therefore ROC curves are, in essence, reflections of the likelihood ratio associated with a given set of test results. ROC regression methods attempt to maximize the ROC curve at each point (maximizing the likelihood ratio for each test cutoff value). Therefore ROC techniques are able to produce the optimal rules for any given set of test results.

Regression techniques are approximations; for ROC regression, the approximation is to the empiric ROC curve. The empiric AUC (area under the curve) represents the optimal solution for a given set of tests. For large studies using multiple test results and covariates, the solution to the empiric ROC requires near impossible calculation power. Therefore approximation methods are needed. (Ma and Huang, 2005; McIntosh and Pepe, *Biometics*, 58 657-664 (2002)). One of the best methods is the sigmoid function approximation to the empiric ROC curve (Ma and Huang, 2005). Partial ROC regression maximizes the ROC curve within clinically acceptable limits of specificity (usually 95% to 100%).

While logistic regression can attempt to approximate the empiric ROC curve over the entire ROC space, only partial ROC regression is able to maximize a portion of the curve; the clinical impact of this nuance is that partial ROC regression using a sigmoid function is better at choosing tests that produce high levels of specificity, while maintaining sensitivity. Penalized likelihood functions may also be employed using the LASSO technique with an $L_1$ penalty to choose the best tests among highly correlated methods. (Kim and Kim, "Gradient LASSO for feature selection," *Proceedings of the 21st Internation Conference on Machine Learning*, Banff, Canada, (2004)). By optimizing the number of tests, the specific tests chosen, and the rules used to combine those tests, it is possible to maximize the likelihood ratio at each point of the partial ROC curve.

Logistic regression using a log-likelihood method provides a good approximation to the empiric ROC curve, though imperfect in areas requiring high specificity (McIntosh and Pepe, 2002); good agreement has been demonstrated between log-likelihood and ROC methods for the CDC dataset (Bacon et al. 2003) used to confirm the inventive methodology. Regardless of the value of logistic methods using small sample sizes, picking the correct variables for evaluation of large samples is critical for performance reasons and cost (Pepe and Thompson, *Biostatist.*, 1(2), 123-140 (2000)).

Partial ROC regression is theoretically superior to logistic regression because of its inherent ability to maximize a portion of the ROC curve. Because logistic regression methods are computationally easier and because of the need to compare multiple predictive models, logistic methods were chosen for the remainder of our analyses. (McIntosh and Pepe 2002). However, the above theoretical reasons predict that for some data sets, ROC regression will produce superior results, either by picking better tests or by using more efficient rules to maximize the critical portion of the ROC curve.

It is not sufficient to choose other regression methods that might produce results superior to current two-step techniques. Rather the ability to choose the best antigens is key, both from a therapeutic and cost perspective. The present invention helps other regression methods learn the correct antigens to use to achieve specificity and sensitivity goals, allowing them to recalibrate more accurately. Both because of theoretically superior overall performance and the ability to improve other techniques, partial ROC regression using a sigmoid approximation and penalized likelihood functions is an optimal means to both choose tests and produce optimal rules to combine tests. Techniques like logistic regression can utilize those features (variables) selected by partial ROC methods to optimize its selection of beta coefficients, thereby enhancing its predictive power.

Rules based on likelihood ratios produce outputs that can be easily combined with pretest probability results through Bayes' Theorem. By multiplying the pretest odds times the likelihood ratio, one generates the post-tests odds, specific to that patient and their test results. The present invention uses an algorithm to determine the pretest probability of disease based on the signs and symptoms of disease. The method described in U.S. Pat. No. 6,665,652 and a new literature review helped formulate the estimates in Table 1. For example, the pretest probabilities listed below can be used in to optimize prediction of LD. Similar pretest probabilities and algorithms can be generated for other diseases without risky experimentation.

Although it is possible to use a likelihood ratio alone to categorize patients as having disease or not, combining clinical and laboratory results has demonstrated even more impressive performance relative to the CDC's 2-tier method. All tests seem to benefit from including information about the pretest risk of infection, but ROC and logistic regression seem to produce the best overall results when combined with pretest risk assessment.

The multivariate method of the present invention is used to select the optimum test panel for disease diagnosis, weight those results to maximize sensitivity and specificity, and ultimately choose a cutoff value for the posttest probability of disease that minimizes the regret associated with false positive and false negative test results. Component laboratory tests identified by the predictive model as critical for diagnosis can be manufactured in the form of test kits with the test panel components incorporated into a microtiter plate to be analyzed by a commercial laboratory.

The laboratory will utilize reading equipment and software provided by the present invention to collect and interpret test data, generating a likelihood ratio for each patient. According to one embodiment of the present invention, the commercial laboratory will electronically transfer each patient's likelihood ratio to their physician's office, to be received by software provided by the present invention for a computer or personal digital assistant. The physician will then evaluate each patient's individual signs and symptoms through a clinical algorithm on the office software to determine the pretest probability of disease. Should there be insufficient information to generate such a score, then the physician may choose to accept the laboratory-derived likelihood ratio for that patient and cutoff value as the final report.

The physician's software will combine the patient's likelihood ratio with the pretest probability of Lyme disease as determined by the physician, generating a posttest probability of Lyme disease. The physician's software will generate a report, including the above results and an interpretation of posttest probability of disease as it relates to the cutoff level we provide. Test results exceeding the cutoff level will help determine whether the patient requires additional tests or treatment for Lyme disease.

The test kit containing the component tests and interpretive clinical and laboratory software, plus the test kit reader, will be marketed as a single test to be FDA approved.

The present invention thus also provides diagnostic software containing code embodying a computer-based method for scoring results from the optimum test panels according to the weights assigned each test or combination thereof and comparing the results against the assigned cutoff value to render a positive or negative diagnosis. Optimum test panel kits are also provided, including kits in which the diagnostic software is included. Methods for diagnosing disease with the test panels and software are also provided.

The multivariate method of the present invention is performed as a computer-based method. The input, processor and output hardware and software other than that expressly described herein is essentially conventional to one of ordinary skill in the art and requires no further description. The input, processor and output hardware employed by computer based methods for diagnosing disease constructed from information derived by the multivariate method of the present invention are also essentially conventional to one of ordinary skill in the art and require no further description The foregoing principles are illustrated in the following example in the context of LD, however, it should be understood that the inventive method can also be applied to other diseases for which there exists multiple diagnostic tests such as connective tissue diseases, Rocky Mountain Spotted Fever, *Babesia microti*, and *Anaplasma granulocytophilia*. Diagnostic testing panels can be developed for each of the foregoing against a test population according to the methods described herein incorporating pretest clinical information to select the optimum test panel for disease diagnosis, the weight to assign each test of combination thereof, and cutoff values that minimize regret associated with false positive and false negative results. For example, the inventive method can be applied to a diagnostic test panel for the diagnosis of Lupus erythematosis and the ARA diagnostic criteria for Lupus erythematosis can be used to determine the pretest probability of disease.

EXAMPLE

Studies that generated the current predictive models are described below.

The prior probability of LD is related to the prevalence of LD in the community and was set at 1% (Nichol et al., *Ann. Intern. Med.*, 128(1), 37-48 (1998); Goodman and Sonenshine (eds.), *Tick-Borne Diseases of Humans*, (ASM Press, Washington, D.C. (2005)). A clinical algorithm to determine the pretest probability of LD, given a patient's clinical signs and symptoms in an endemic area, will be discussed below.

Partial ROC regression and logistic regression analyses were performed on a CDC database of LD patients (n=280) and controls (n=559). In order to combine multiple diagnostic tests, a linear combination of test results was used to create a score function. In this case the score for each patient was a likelihood ratio (LR) based on their individual test results. The empiric AUC was approximated for the $(1-t_0)$ quantile of patients without LD, where $t_0$ represents the maximum acceptable false-positive rate (Pepe and Thompson, 2000; Dodd and Pepe, *Biometrics*, 59, 614-623 (2003)). Quantiles between 80% and 100% specificity and 95% to 100% specificity were evaluated.

This partial ROC curve was smoothed using a sigmoid function as the indicator function. Tests with significant independent contributions and their accompanying β values were chosen using a LASSO technique with an $L_1$ penalty ((Ma and Huang, 2005; Kim and Kim, 2004).

The partial ROC area under the curve was used to define the diagnostic performance of non-binary tests. Secondary evaluations compared the sensitivity of each method at a fixed specificity of 99% (specificity of the two-tier method) and the specificity of each method at a fixed sensitivity of 67.5% (the sensitivity of the two-tier method). Comparisons between the AUCs created by the different methods were performed using a bootstrap technique. A binary combination of C6 IgG and pepC10 IgM antibodies had been evaluated using this database. The results from this binary combination were also compared to the alternative methods using sensitivity and specificity parameters. Confidence intervals were determined using a bootstrap technique.

After a score function was created, a unique clinical algorithm was used to determine the pretest risk of Lyme disease among patients presenting with various syndromes. The principal diagnosis assigned by the patient's primary physician was used to help generate the pretest probability, in conjunction with the data obtain through a literature review and the methods detailed in U.S. Pat. No. 6,665,652. All patients and controls presenting with similar syndromes were assigned the following identical pretest probabilities:

| | Pretest probability of Lyme disease (range)[a] | |
|---|---|---|
| 1) | Influenza-like illness | 0.110 (0.070-0.145) |
| 2) | Pauci-articular arthritis | 0.065 (0.042-0.095) |
| 3) | Chronic encephalopathy | 0.035 (0.020-0.069) |
| 4) | Radiculopathy | 0.041 (0.020-0.060) |
| 5) | Facial palsy (adults) | 0.139 (0.065-0.222) |
| 6) | Facial palsy (children) | 0.390 (0.065-0.660) |
| 7) | Aseptic meningitis | 0.077 (0.048-0.137) |
| 8) | EM-compatible[b] rash | 0.685 (0.051-0.830) |
| 9) | Asymptomatic ANA[c] | 0.010 (0.005-0.020) |
| 10) | Asymptomatic RF[d] | 0.020 (0.010-0.030) |
| 11) | Healthy blood donor[e] | 0.010 (0.005-0.020) |

[a]Method of U.S. Pat. No. 6,665,652 and literature review; prospective studies used if available. If 2 or fewer studies, range chosen 50-100% higher and 50% lower.
[b]EM; erythema migrans
[c]ANA; anti-nuclear antibody
[d]RF; rheumatoid factor
[e]Community incidence of disease is higher than true value for this set of patients, but was used to challenge the diagnostic abilities of the model.

The pre-test probability (p) was changed into a pretest odds ratio p/(1−p). The pre-test odds times the LR for each patient produced a post-test odds ratio. The post-test odds ratio was converted into a probability format through the formula Odds/(1+Odds).

Partial ROC curves were created for each predictive model, including the two-step method, single kinetic-EIA assays, the binary combination of C6 IgG and pepC10 IgM, and two multivariate methods (partial ROC regression and logistic regression) by varying their respective posttest cutoff values. The AUCs of the partial ROC curves were compared as described above and served as a metric for test performance. ROC curves cannot be accurately generated when binary tests (including the two-tier) are used before combining with pre-test probabilities. Sensitivity at a fixed specificity and specificity at a fixed sensitivity were used in these cases for test comparison (Pepe 2003).

Figure 2:
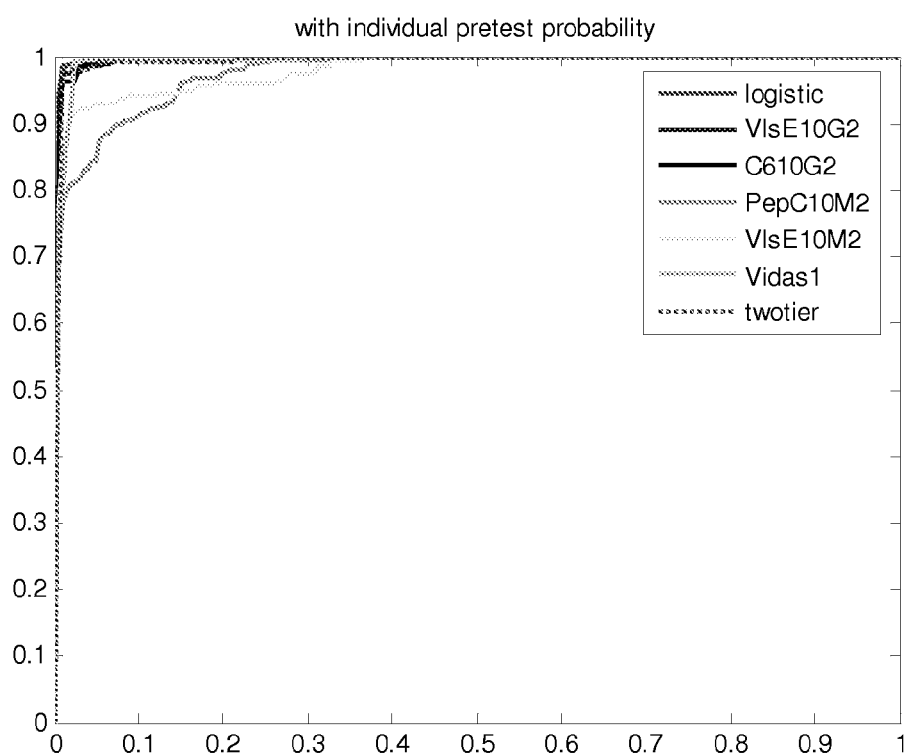
FIG. 2 depicts an ROC plot based on posttest probability using individual pretest probability derived from clinical information for five Lyme Disease assays.
Figure 3:
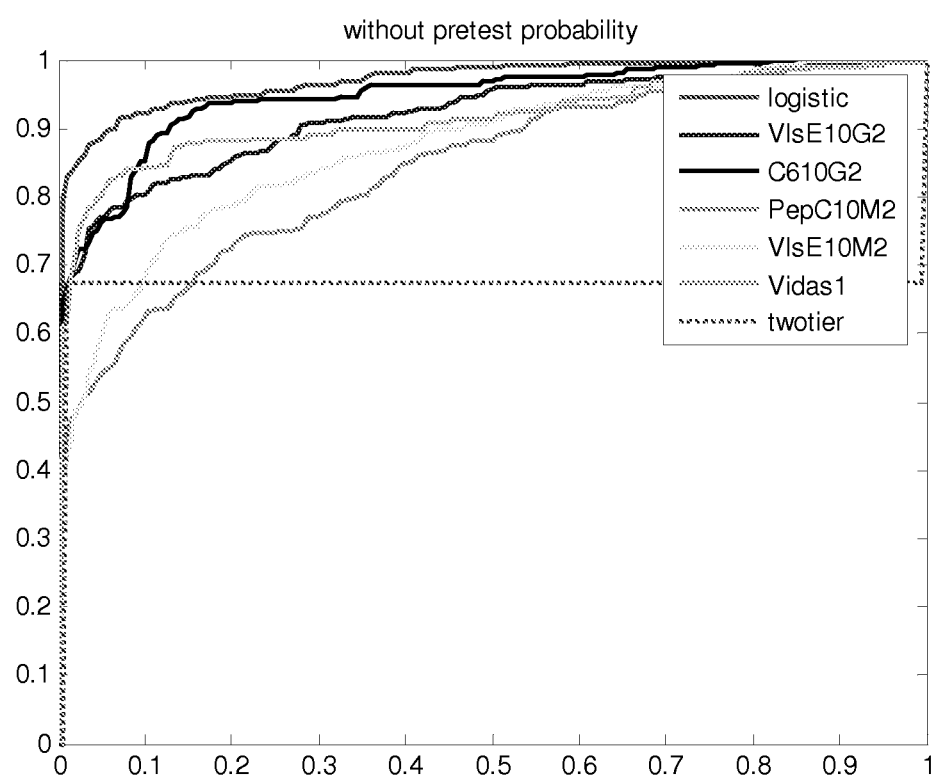
FIG. 3 depicts an ROC plot based on likelihood ratio without pretest probability.

The results are detailed in Tables 1 to 4 and FIGS. 1 to 3. FIGS. 1 to 3 show that the logistic score is superior to the two-tier method and single antibody tests; however, this logistic method combined all five assays to generate these results. Further ROC and logistic analysis demonstrated that using three antibodies with one interaction term was non-inferior to using five antibodies, and that both multivariate methods utilized the same three antibodies for a predictive model.

The beta-coefficients for V1sE1 IgG, C6 IgG, pepC10 IgM, and the C6/pepC10 interaction term were 8.922, 25.09, 10.77, and 1.00, respectively, for partial ROC regression (80% to 100% specificity). These coefficients indicate strong diagnostic contributions by each variable. Logistic regression using three antibodies with one interaction term was utilized for subsequent analyses because of computational ease, although slightly less powerful than raw ROC regression scores using the same features (data not shown).

TABLE 1

Laboratory performance of two-tier vs. logistic score: sensitivity at a fixed specificity (Bacon et al. 2003)[c]

|  | Sensitivity[d] | Specificity |
|---|---|---|
| Logistic score[a] | 0.795 (0.614) | 0.991 |
| Two-tier | 0.675 (0.375) | 0.991 |
| Absolute difference | 0.119 (0.239) | NA[e] |
| 95% Confidence interval[b] | 0.054 to 0.177 (0.123 to 0.352) | |

[a]Combination of C6 IgG, VlsE1 IgG, and pepC10 IgM with C6 IgG-pepC10 IgM interaction
[b]Bootstrap method used
[c]Entire dataset used, all time points. No pretest probabilities used
[d](Early acute Lyme disease)
[e]NA; not applicable

TABLE 2

Laboratory performance of two-tier, binary C6 IgG or pepC10 IgM, and logistic score: specificity at a fixed sensitivity (Bacon et al. 2003)[d]

|  | Sensitivity | Specificity |
|---|---|---|
| Logistic score[a] | 0.675 | 0.998 |
| Two-tier/binary | 0.675 | 0.991/0.979 |
| Absolute difference | NA[c] | 0.007/0.0197 |
| 95% Confidence interval[b] | NA | (0.002 to 0.014)/(0.009 to 0.032) |

[a]Combination of C6 IgG, VlsE1 IgG, and pepC10 IgM with C6 IgG-pepC10 IgM interaction
[b]Bootstrap method used.
[c]NA; not applicable
[d]Entire dataset used, all time points. No pretest probabilities used.

TABLE 3

Combined clinical and laboratory performance by partial ROC area[d,e]

|  | AUC 80%-100% | AUC 95%-100% |
|---|---|---|
| Logistic method[a] | 0.996 | 0.983 |
| Two-tier/Binary[b] | 0.975/0.952 | 0.923/0.885 |
| Absolute difference | 0.011/0.044 | 0.060/0.095 |
| 95% Confidence Interval[c] | (0.01-0.02)/(0.04-0.07) | (0.01-0.13)/(0.04-0.17) |

[a]Combination of C6 IgG, VlsE1 IgG, and pepC10 IgM with C6 IgG-pepC10 IgM interaction
[b]Binary combination of C6 IgG or pepC10 IgM reported next to 2-tier for partial AUC, difference in AUC with logistic method, and 95% confidence interval of that difference.
[c]Bootstrap method used
[d]80-100% and 95-100% AUCs normalized by dividing by 0.2 and 0.05, respectively
[e]Posterior probabilities derived using pretest probabilities and likelihood ratios; ROC created by varying the posterior probability cutoff value; entire dataset used, all time points

TABLE 4

Combined clinical and laboratory performance: sensitivity at a fixed specificity[e]

|  | Sensitivity | Specificity |
|---|---|---|
| Logistic score[a] | 0.997 | 0.980 |
| Two-tier/binary | 0.981/0.959 | 0.980 |
| Absolute difference | 0.016/0.038 | NA[c] |
| 95% Confidence interval[b] | NS[d]/(0.014-0.062) | NA |

[a]Combination of C6 IgG, VlsE1 IgG, and pepC10 IgM with C6 IgG-pepC10 IgM interaction
[b]Bootstrap method used, no significant difference.
[c]NA; not applicable
[d]NS; not significant (0.0 to 0.033)
[e]Entire dataset used, all time points.

Tables 1 to 4 demonstrate significant gains in sensitivity, specificity, and AUC performance over the two-tier method and binary combination of C6 IgG and pepC10 IgM by combining the three antigens above through multivariate means. These results were not expected, even by the expert participants in the Bacon 2003 study. A significant role was confirmed for V1sE1, which should be used along with the other two antigens in a new test.

The use of these three antibodies, V1sE1 IgG, C6 IgG, and pepC10 IgM was optimized using ROC and logistic regression. When individual pretest probabilities were combined with raw logistic and ROC scores, the AUCs for both methods increased by nearly 10%. Table 4 demonstrates that both the logistic method and the two-tier method experience significant gains in sensitivity of 19% and 27%, respectively, by adding clinical information to the laboratory data. There was no loss of specificity (99%).

Although the above data demonstrates that ROC and logistic regression can improve overall laboratory performance compared to the two-tier method, the differences between these methods and the two-tier method diminish as a consequence of combining them with the clinical algorithm. A cutoff value may be chosen after an optimized diagnostic method is studied using a prospective validation dataset. The prospective validation set preferably consists of patients and controls prospectively selected to meet the 1991 FDA requirements for devices to diagnose Lyme disease.

The point on the optimized ROC curve that intersects a line with the slope $(1-p)\cdot C/[p\cdot B]$ will define the test cutoff value for the validation set, where p in the prevalence of LD in the validation set, B is the regret associated with false-negative results and C is the regret associated with false-positive results. If the validation set approximates that seen by primary care physicians, then the population prevalence of LD in that set may help define an optimal cutoff value for diagnostic purposes. Alternatively, one may define p as the prevalence of LD in the population at large.

The ratio of regret from not treating someone with early LD to that from treating someone without LD is calculated as follows. The regret associated with false-negative serology is the difference in utility between false-negative and true-positive states; the regret associated with false-positive serology is the different in utility between the true-negative and false-positive states (i.e. utility lost due to treatment for Lyme disease). Those with false-negative tests are assumed to come to the attention of physicians about 80% of the time (Rahn, *Lyme Disease* (Philadelphia: American College of Physicians, 1998)), usually with arthritis (60%), neurological disease (15%), or cardiac disease (5%) (Goodman 2005). Treatment failure rates were estimated as 15% for arthritis, 10% for neurological and cardiac disease, and 5% for early LD (Shadick et al., *Arch. Intern. Med.*, 161(4), 554-61 (2001)).

Regret was estimated by prior LD patients using a visual analog scale; disutility values were 0.20 during treatment for early LD or false-positive serology, 0.31 for arthritis treatment, and 0.40 for other disease or failure states (Shadick 2001). Failure states were assumed to last 5 years and regret was discounted by 3% yearly. It was assumed that all patients diagnosed with disease or who had positive tests were treated for at least one month. Based on the above assumptions, the calculated regret ratio (regret due to false-negatives/regret due to false-positives) is 13.8. If patients with false-positive serology are treated for three months instead of one month (a non-standard approach (Reid et al., *Ann Intern. Med.*, 128(5), 354-62 (1998)), then the regret ratio falls to 4.6.

Additional data suggests the value of this approach when using the Western blot for Lyme disease diagnosis. The same CDC database used to construct the EIA predictive model was available for Western blot analysis.

There were 280 patients with disease in the study described above (Bacon et al. 2003), of whom 80 had early acute disease and 106 had early convalescent disease. These are the hardest patients to diagnose. The same 559 controls were used as in Bacon (2003). Patients initially positive or equivocal by the VIDAS EIA were evaluated using the IgG and IgM Western blots, performed and interpreted using CDC standards; the goal of this analysis was to separate true-positive from false-positive serology. All IgG and IgM bands were used simultaneously for any given group of patients; each band result was interpreted in a binary fashion.

For each group a score was derived using backward stepwise logistic regression. For both early acute disease and early convalescent disease, the logistic score was more sensitive than the standard Western blot at confirming true-positive serology; there was no loss of specificity. For early acute disease, the logistic score confirmed 40/47 (85%) true-positive cases compared to 30/47 (64%) cases using the standard CDC interpretation (p=0.032 by two-tailed Fisher's exact test). Both methods demonstrated 99% specificity for the overall control panel.

For early convalescent disease, the logistic score confirmed 83/96 (86%) of patients with true-positive serology, versus 71/96 (74%) using the standard CDC Western blot interpretation (p=0.045 by two-tailed Fisher's Exact test). Both methods were 99% specific.

Instead of the usual 13 bands, the logistic score was able to use only 8 bands to confirm early disease, and only 6 bands to confirm late disease; this demonstrates more efficient use of data. The most important band for separating true-positive from false-positive serology was the 39-kDa band (i.e. the highest beta coefficient in the logistic formula). The name of the principle protein in this band is BmpA. This data suggests that BmpA might be valuable to include in a new recombinant and peptide-antigen test panel.

A new technique used to determine if a Western blot band is positive or negative is called densitometry. The density of the band is measured and a cutoff value assigned. The band is then reported as either present of absent. The multivariate technique described above may be improved by using continuous rather than binary data for the Western blot bands. Continuous data provides more information to use in the multivariate analysis and may well improve the diagnostic power of the multivariate technique compared to using binary data for the Western blot bands.

The above results were obtained without using Bayesian methods (i.e. pretest and posttest probabilities). Including pretest risk assessment would likely improve upon these results, but it is not a requirement to produce a workable test. The fact that the same multivariate methodology is applicable to different types of tests speaks to its broad application.

The above approach may be applied to any disease where multiple tests may aid in diagnosis, and standardized clinical assessment is utilized. Alternative multivariate predictive models can learn from the ROC model by choosing the same variables as those derived from partial ROC regression methods and then optimizing their beta coefficients.

The inventive method can be applied to other tick-borne diseases such as Rock Mountain Spotted Fever, and the like. The method is suitable for essentially any differential diagnosis type disease condition, and is particularly well-suited for application to cancer diagnosis techniques such as clinical proteomics, where the number of variables is unusually high relative to the number of patients studies. Specificity is of high value and choosing tests and beta-coefficients to maximize the partial ROC curve at 95% to 100% specificity may be very helpful diagnostically or prognostically.

The following above-cited references are incorporated herein by reference in their entirety:

REFERENCES

Donta S T. Tetracycline therapy for chronic Lyme disease. Clin Infect Dis 1997 July; 25 Suppl 1:S52-56.

Wormser G P, Dattwyler R J, Shapiro E, et al. Reply to Pollack, Donta, Wilson, and Arenaz. Clin Infect Dis. 2007; 44:1137-1139.

Trevejo R T, Krause P J, Sikand V K, et al.: Evaluation of two-test sero-diagnostic method for early Lyme disease in clinical practice. J Infect Dis 1999; 179(4): 931-8.

Porwancher R. Improving the specificity of recombinant immunoassays for lyme disease. J Clin Microbiol 2003; 41(6): 2791.

Bacon R M, Biggerstaff B J, Schriefer M E, et al.: Serodiagnosis of Lyme disease by kinetic enzyme-linked immunosorbent assay using recombinant V1sE1 or peptide antigens of *Borrelia burgdorferi* compared with 2-tiered testing using whole-cell lysates. J Infect Dis 2003; 187(8): 1187-99.

Honegr K, Havlasová J, Gebouský P, et al. Criteria for the evaluation of the immunoblot in the diagnosis of Lyme borreliosis using *Borrelia afzelii*, *Borrelia garinii*, and *Borrelia burgdorferi* sensu stricto. Epidemiol. Mikrobiol. Immunol. 2001; 50(4):147-156. [article in Finnish]

Robertson J, Guy E, Andrews N, et al.: A European multicenter study of immunoblotting in serodiagnosis of lyme borreliosis. J Clin Microbiol 2000; 38(6): 2097-102.

Guerra M A, Walker E D, Kitron U: Quantitative approach for the sero-diagnosis of canine Lyme disease by the immunoblot procedure. J Clin Microbiol 2000; 38(7): 2628-32.

Neyman J, Pearson E S. On the problem of the most efficient tests of statistical hypothesis. Philosophical Transactions of the Royal Society of London, Series A. 1933; 231: 289-337.

Pepe M S: The Statistical Evaluation of Medical Tests for Classification and Prediction, First Edition ed. Oxford, U.K.: Oxford University Press, 2003.

Ma S, Huang J. Regularized ROC estimation: with applications to disease classification using microarray data. June 2005, University of Iowa, Department of Statistics and Actuarial Science, Technical Report No. 345.

McIntosh M W, Pepe M S. Combining several screening tests: optimality of the risk score. Biometics 2002; 58:657-664.

Kim Y, Kim J. Gradient LASSO for feature selection. *Proceedings of the 21st Internation Conference on Machine Learning*, Banff, Canada, 2004.

Pepe M S, Thompson M L. Combining diagnostic test results to increase accuracy. Biostatistics 2000; 1(2):123-140.

Nichol G, Dennis D T, Steere A C, et al.: Test-treatment strategies for patients suspected of having Lyme disease: a cost-effectiveness analysis. Ann Intern Med 1998; 128(1): 37-48.

Goodman J L D D, Sonenshine D E (eds.): Tick-Borne Diseases of Humans 2005; ASM Press: Washington, D.C.

Dodd L E, Pepe M S. Partial AUC estimation and regression. Biometrics 2003; 59:614-623.

Rahn D W: Lyme Disease. Philadelphia: American College of Physicians, 1998.

Shadick N A, Liang M H, Phillips C B, Fossel K, Kuntz K M: The cost-effectiveness of vaccination against Lyme disease. Arch Intern Med 2001; 161(4): 554-61.

Reid M C, Schoen R T, Evans J, Rosenberg J C, Horwitz R I: The consequences of overdiagnosis and overtreatment of Lyme disease: an observational study. Ann Intern Med 1998; 128(5): 354-62.

As will be readily appreciated, numerous variations and combinations of the features set forth above can be utilized without departing from the present invention as set forth in the claim. Such variations are not intended as a departure from the spirit and scope of the invention, and all such variations are intended to be included within the scope of the following claims.

What is claimed is:

1. A kit comprising a diagnostic test panel for diagnosing Lyme disease and a non-transitory computer program product comprising software which comprises code for interpreting test results from the diagnostic test panel, wherein the code is configured to cause a computer to perform steps comprising:

(a) receiving results from performing the diagnostic test panel on a test population comprising a statistically significant sample of individuals with at least one objective sign of Lyme disease and a statistically significant control sample of healthy individuals or persons with cross-reacting medical conditions;

(b) generating, by the computer, a score function from a linear combination of said diagnostic test panel results, said linear combination expressed as $\beta^T Y$, wherein D is Lyme disease; $Y_1, \ldots, Y_k$ is a set of K diagnostic tests for D; Y is a vector of diagnostic test panel results $\{Y_1, \ldots, Y_k\}$; D'=not D; $\beta$ is a vector of coefficients $\{\beta_1, \ldots, \beta_k\}$ for Y; and $\beta^T$ is the transpose of $\beta$;

(c) performing, by the computer, a receiver operating characteristic (ROC) regression or alternative regression technique of the score function, wherein $\beta$ coefficients are calculated to maximize the area under the curve (AUC) of the empiric ROC as approximated by:

$$AUC(\beta) = \frac{1}{n^D \cdot n^H} \sum_{i \in D, j \in D} I(\beta^T Y_i > \beta^T Y_j),$$

wherein I is an indicator function, N=the number of study subjects, $n^D$ is the number of patients with Lyme disease D, $n^H$ is the number of healthy controls, $n^D + n^H = N$; i=1, ..., $n^D$, i ∈ D are patients with Lyme disease; j=1, ..., $n^H$, j ∈ H are healthy controls;

(d) calculating, by the computer, for each individual the pre-test odds of Lyme disease;

(e) generating a diagnostic likelihood ratio of Lyme disease by determining the frequency of each individual's test score in said diseased population relative to said control population, (f) multiplying said pretest odds by said likelihood ratio to determine the post-test odds of Lyme disease for each individual;

(g) converting, by the computer, a set of posttest odds into posttest probabilities for each methodology and creating an ROC curve for each methodology by altering its respective post-test probability cutoff value;

(h) comparing, by the computer, the ROC areas generated by one or more regression techniques to determine an optimal methodology, comprising tests included in the diagnostic test panel and the weight to be assigned each test score alone or in combination;

(i) dichotomizing, by the computer, the optimal methodology by finding that point on the final ROC graph tangent to a line with a slope of (1−p)C/p·B, where p is the population prevalence of Lyme disease, B is the regret associated with failing to treat patients with Lyme disease and C is the regret associated with treating a patient without Lyme disease, thereby generating a posttest probability cutoff value; and (j) displaying, by the computer, an optimized diagnostic test panel for Lyme disease diagnosis, wherein the weight each individual test score is to be assigned alone or in combination, and the cutoff value against which positive or negative diagnoses are to be made.

2. The kit of claim 1, wherein said diagnostic test panel comprises one or more of a test for the V1sE1 IgG antibody, a test for the C6 IgG antibody, a test for the pepC10 IgM antibody, and a test for an antibody to the BmpA peptide.

3. The kit of claim 1, wherein $t_0$ is the maximum false-positive rate desired by a physician interpreting the diagnostic test panel and is a multiple of $1/n^H$, and the $\beta$ coefficients are chosen through partial ROC regression, so that the largest area below the partial ROC curve for the $(1-t_0)$ quantile of individuals without D is generated, wherein $\beta^T Y_j > c$ and the survival function of patients without Lyme disease with a score of c, $S_H(c)$, is equal to $t_0$.

4. The kit of claim 1, wherein the ROC curve is smoothed using a sigmoid function:

$$S(x) = 1/[1 + \exp(-x)],$$

wherein bias is decreased in estimating x values close to zero by introducing a series of positive numbers $\sigma_n$, satisfying the condition that $\sigma_n$ approaches zero as n approaches infinity, such that $S_n(x) = S(x/\sigma_n)$, wherein the optimal $\beta$ is determined using the sigmoid approximation as the sigmoid maximum rank correlation estimator:

$$\beta(\text{optimal}) = \text{argmax}\left\{R_n(\beta) = \frac{1}{n^D \cdot n^H} \sum_{i \in D, j \in H} S_n[\beta^T(Y_i - Y_j)]\right\},$$

wherein a LASSO tuning parameter, $L_1$ constraint $\leq u$, is determined using a V-fold cross validation technique.

5. The kit of claim 1, wherein the optimized score function $\beta^T Y$ generates a score, $c_i$ for each patient i with D, and $c_j$, for each control patient j, wherein the likelihood ratios for scores $c_i$ and $c_j$, $P(c_i/D)/P(c_i/D')$ and $P(c_j/D)/P(c_j/D')$, respectively, are monotone increasing in patients with D.

6. The kit of claim 1, wherein when there is insufficient data to determine the pretest risk that a patient has D (Lyme disease) and a laboratory reports the likelihood ratio and cutoff value for that patient's test results directly to the physician, the cutoff value for the likelihood ratio is determined by observing the likelihood ratio resulting in 99% specificity in a control population of patients and likelihood ratios that exceed the cutoff value thus derived indicate that there is a high probability of D (Lyme disease).

7. The kit of claim 1, the pretest risk of D is calculated using an individual's clinical signs and symptoms.

8. The kit of claim 1, wherein the pretest risk of D is calculated using the distribution of Lyme disease manifestation in the population from which said individuals are selected.

9. The kit of claim 1, wherein the posterior odds of D are calculated by multiplying the pretest odds of D by the likelihood ratio associated with the score generated by the patient's diagnostic test panel results; and where the posterior odds of D are converted into the posttest probability of D by calculating odds/[1+odds].

10. The kit of claim 1, wherein an ROC regression approximation is performed in step (c) and is selected from logistic regression, log-likelihood regression, linear regression, or discriminant techniques.

11. The kit of claim 1, further comprising the step of substituting at least a portion of said optimal methodology in another multivariate regression technique using less optimum methodology.

12. The kit of claim 11, wherein said multivariate regression technique is selected from logistic regression, log-likelihood regression, linear regression, or discriminant techniques.

* * * * *

UNITED STATES PATENT AND TRADEMARK OFFICE
CERTIFICATE OF CORRECTION

PATENT NO. : 8,694,265 B2
APPLICATION NO. : 13/184017
DATED : April 8, 2014
INVENTOR(S) : Richard Porwancher It is certified that error appears in the above-identified patent and that said Letters Patent is hereby corrected as shown below:

In the Specification

Column 1, lines 15-18, replace,
"This invention was made with government support under Grant No. 1R43AI069564-01 which was awarded by the National Institute of Allergy and Infectious Diseases (NIAID). The government has certain rights in the invention."
with,
"This invention was made with government support under grant AI069564 awarded by the National Institutes of Health. The government has certain rights in this invention."

Column 5, lines 27-32, replace the equation:
$$AUC(\beta) = \frac{1}{n^D \cdot n^H} \sum_{i \in D, j \in D} I(\beta^T Y_i > \beta^T Y_j),$$
" with the equation:

$$AUC(\beta) = \frac{1}{n^D \cdot n^H} \sum_{i \in D, j \in D} I(\beta^T Y_i > \beta^T Y_j),$$
"

Column 5, line 33, replace,
"wherein I is a sigmoid function,"
with,
"wherein I is an indicator function,"

Column 5, line 35, replace,
"number of healthy controls, $n^D + n^H = N$; $i=1, \ldots, n^D$, $i \in D$ are"
with,
"number of healthy controls, $n^D + n^H = N$; $i=1, \ldots, n^D$, $i \in D$ are"

Signed and Sealed this
Second Day of December, 2014

Michelle K. Lee
*Deputy Director of the United States Patent and Trademark Office*

CERTIFICATE OF CORRECTION (continued)
U.S. Pat. No. 8,694,265 B2

Column 5, line 36, replace,

"patients with disease; $j=1,\ldots,n^H$, $j \in H$ are healthy controls;"

with,

"patients with disease; $j=1,\ldots,n^H$, $j \in H$ are healthy controls;"